United States Patent [19]

Meili et al.

[11] Patent Number: 4,694,247
[45] Date of Patent: Sep. 15, 1987

[54] METHOD AND APPARATUS INCLUDING A CUSHION OF PULVERULENT MAGNETIC MATERIAL FOR STRAY FIELD MAGNETIC TESTING OF FERROMAGNETIC PARTS

[75] Inventors: Ernst Meili, Uster; Karl Rimmele, Schmerikon, both of Switzerland

[73] Assignee: MECAPEC S.A., St. Gallen, Switzerland

[21] Appl. No.: 741,812

[22] Filed: Jun. 6, 1985

[30] Foreign Application Priority Data

Jun. 8, 1984 [DE] Fed. Rep. of Germany ....... 3421404
Jun. 25, 1984 [DE] Fed. Rep. of Germany ....... 3423368

[51] Int. Cl.$^4$ .................... G01N 27/84; G01R 33/12
[52] U.S. Cl. .................................. 324/216; 324/226; 324/262
[58] Field of Search .............................. 324/214–216, 324/226, 261, 262

[56] References Cited

U.S. PATENT DOCUMENTS

| | | | |
|---|---|---|---|
| 2,061,692 | 11/1936 | Bagley | 324/216 |
| 2,518,943 | 8/1950 | Schott | 324/216 |
| 3,249,861 | 5/1966 | Pevar | 324/216 |
| 3,609,532 | 9/1971 | Van Kirk | 324/215 |
| 3,614,604 | 10/1971 | Reinshagen | 324/216 |
| 3,668,517 | 6/1972 | Zemberry | 324/216 |
| 3,763,423 | 10/1973 | Forster | 324/216 |

FOREIGN PATENT DOCUMENTS

| | | | |
|---|---|---|---|
| 0033789 | 3/1977 | Japan | 324/216 |
| 0017780 | 2/1978 | Japan | 324/216 |
| 0146157 | 9/1982 | Japan | 324/216 |

Primary Examiner—Gerard R. Strecker
Attorney, Agent, or Firm—Peter K. Kontler

[57] ABSTRACT

Elongated ferromagnetic parts of cylindrical or polygonal cross-sectional outline are tested while rotating about their axes and while advancing longitudinally along a cushion of dry pulverulent magnetic material which is supplied by one or more pneumatic conduits into the range of one pole of a first U-shaped electromagnet whose poles extend in the longitudinal direction of but do not contact the parts. The electromagnet establishes a stray magnetic flux in the region of each defect on the ferromagnetic part which is being tested and such flux or fluxes attract pulverulent material which thereby pinpoints the locations of defects. A second electromagnet is placed next to the one pole of the first electromagnet and its poles are spaced apart from each other as considered in the longitudinal direction of the tested part.

24 Claims, 12 Drawing Figures

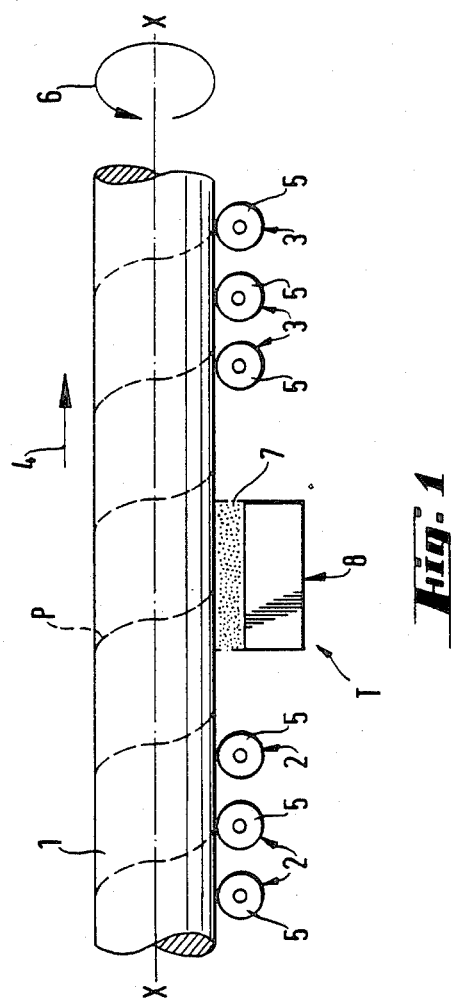

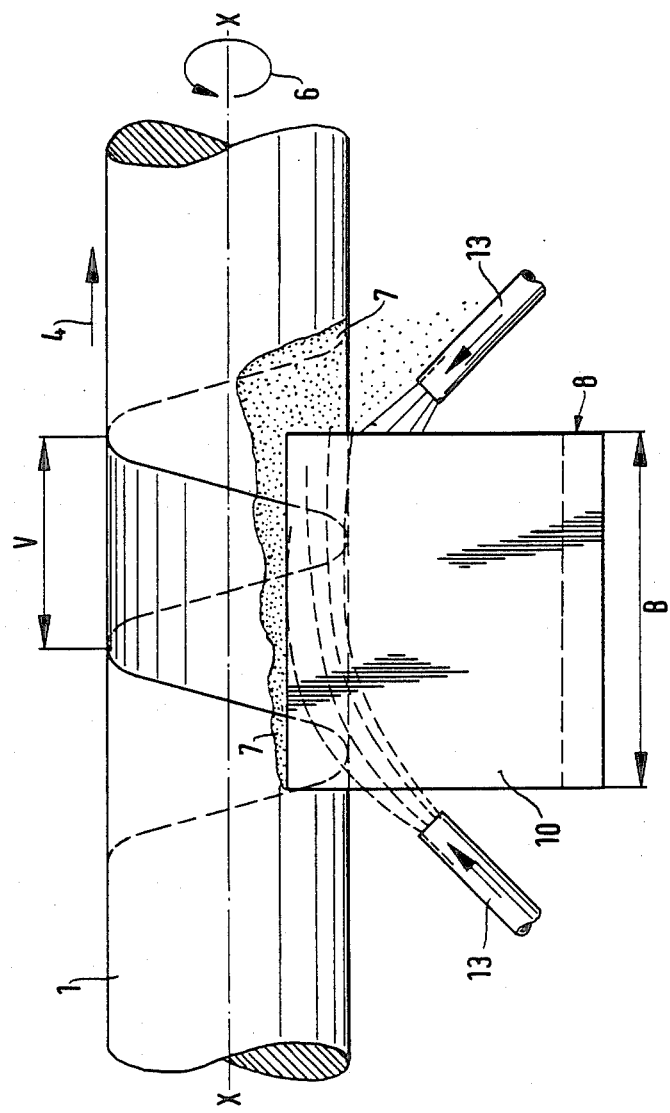
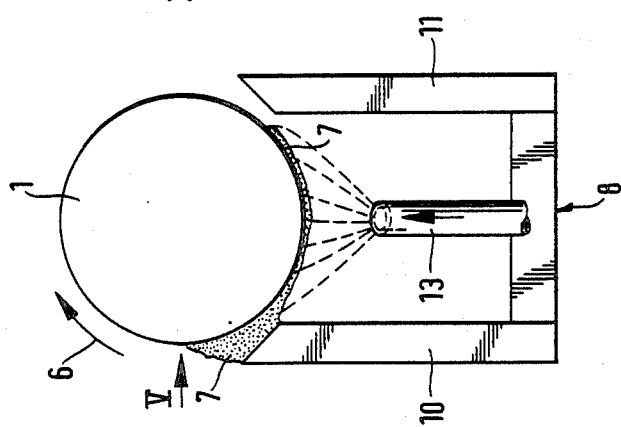

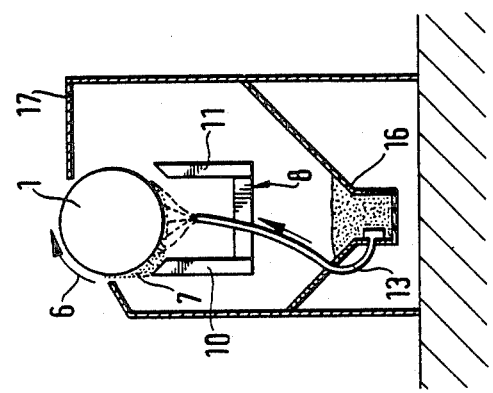
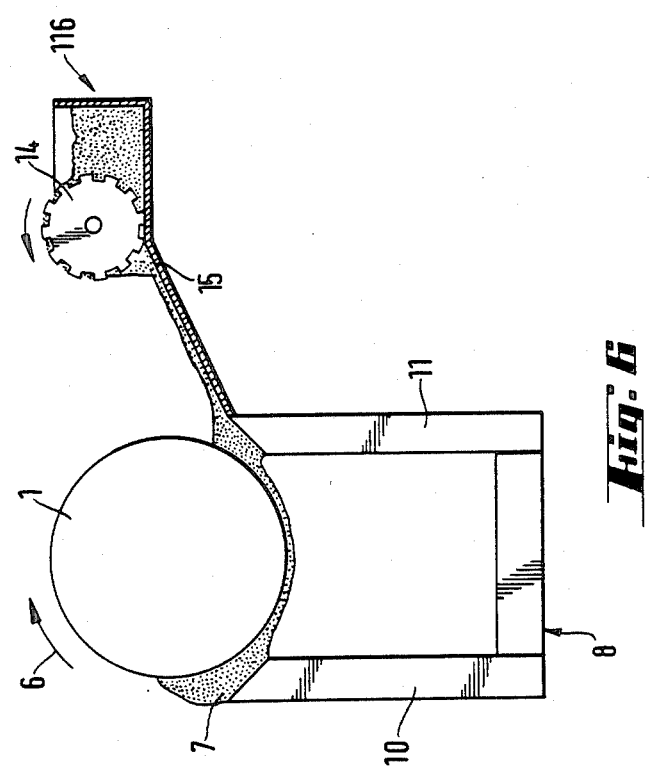

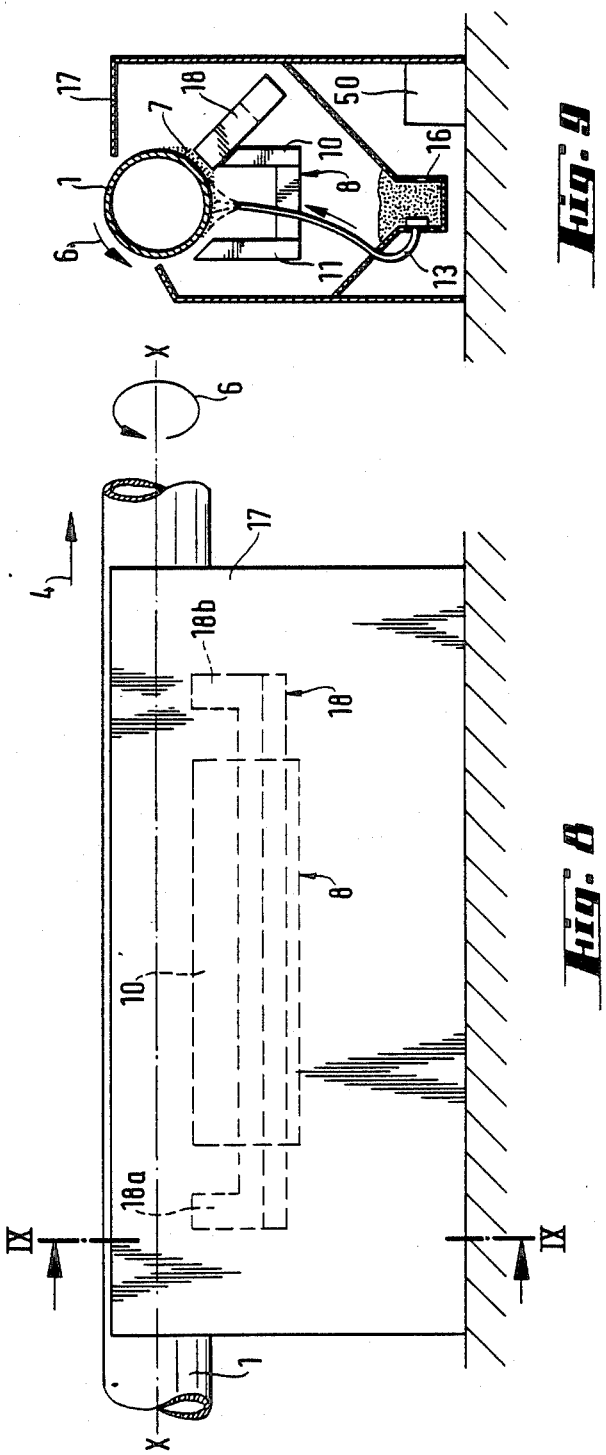

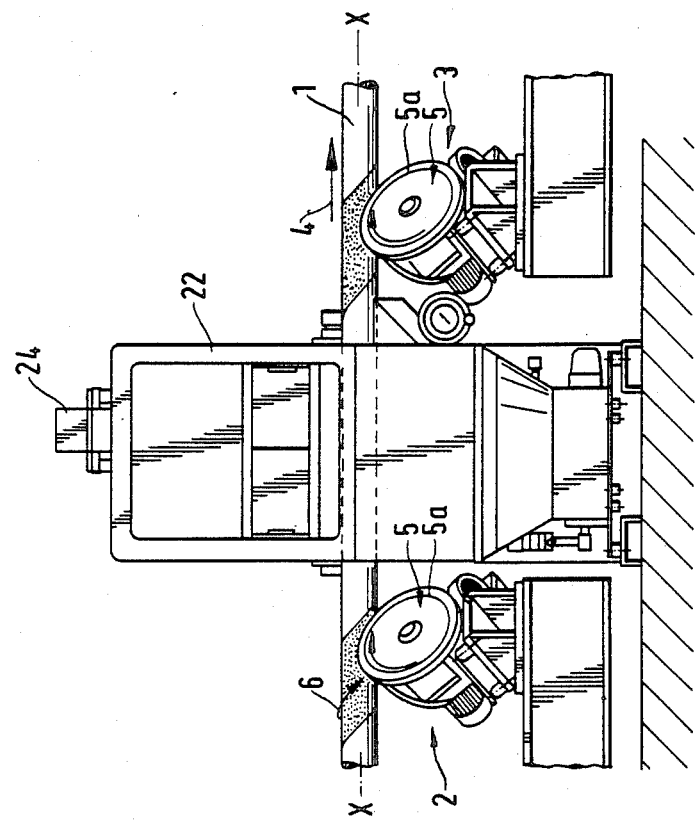
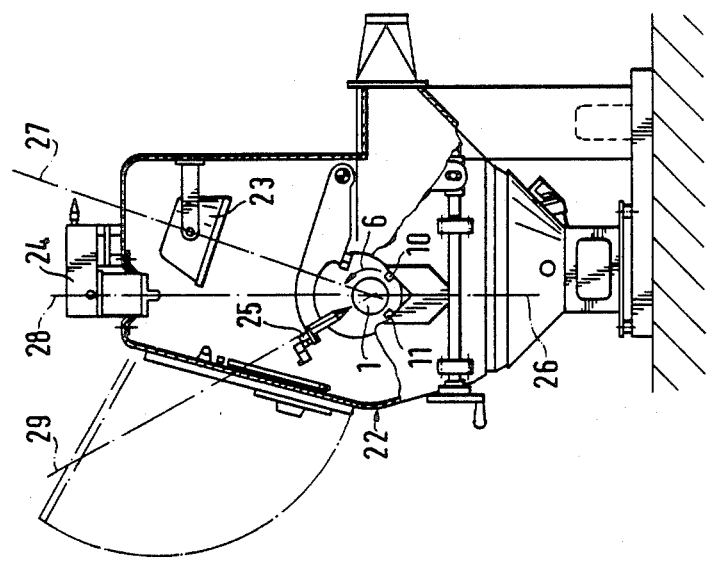

METHOD AND APPARATUS INCLUDING A CUSHION OF PULVERULENT MAGNETIC MATERIAL FOR STRAY FIELD MAGNETIC TESTING OF FERROMAGNETIC PARTS

BACKGROUND OF THE INVENTION

The present invention relates to testing of metallic objects for the presence or absence of defects, and more particularly to improvements in a method and apparatus for so-called stray field or stray flux magnetic testing of elongated ferromagnetic parts.

Stray field magnetic testing involves the placing of a part to be tested into a magnetic field whereby the part develops a stray field in the region of each defect which warrants detection. The stray field attracts a pulverulent magnetic material which is sprayed or otherwise delivered into contact with the part to be tested whereby the material which adheres to the part pinpoints the location of the defect. Such mode of testing ferromagnetic parts is often resorted to in steel making and steel processing plants in order to detect defects in the surface of a semifinished product prior to incurring the expense of further processing. The defects are remedied or the defective parts are segregated from satisfactory parts.

Heretofore known stray field magnetic testing methods and apparatus satisfactory as far as the detection of defects is concerned. However, conventional methods and apparatus often necessitate two or more passes of the parts to be tested through the testing station, or the transport of the parts to be tested through several testing stations, each of which prolongs the testing operation and contributes to its cost. This is due to the fact that, when tested in accordance with heretofore known methods and/or in heretofore known apparatus, all sides of the parts to be tested cannot be simultaneously contacted with a mass of pulverulent magnetic material (e.g., ferritic powder) or all sides cannot be contacted with such material to the same extent.

German Offenlegungsschrift No. 21 16 827 discloses an apparatus for destruction-free testing of ferromagnetic parts in a continuous operation. The apparatus includes means for spraying a magnetic powder emulsion onto the running semifinished part. Such mode of testing creates many problems during actual testing as well as thereafter if all traces of the applied emulsion are to be removed from the surface of the tested commodity. Moreover, the apparatus which is disclosed in the aforementioned Offenlegungsschrift is not suited for the testing of ferromagnetic parts at elevated temperatures, and such apparatus must be provided with several testing stations if the entire peripheral surface of a moving part is to be tested during a single pass through the apparatus. This contributes significantly to the initial and maintenance cost of the apparatus. Reference may also be had to U.S. Pat. No. 3,763,423 granted Oct. 2, 1973 to Förster which discloses an apparatus with two testing stations and means for spraying a magnetic powder emulsion at several locations against selected portions of the advancing part. The apparatus of Förster advances the parts longitudinally while holding the advancing parts against rotation in order to ensure that each discrete spray of magnetic powder emulsion will impinge upon a selected strip-shaped portion of the peripheral surface of the ferromagnetic part.

Another mode of testing a continuously advancing ferromagnetic part in accordance with the stray field magnetic technique is disclosed in European patent application Ser. No. 0 090 190. The apparatus of this application employs dry magnetic powder and is similar to that disclosed in U.S. Pat. No. 3,614,604 granted Oct. 19, 1971 to Reinshagen. Reinshagen proposes to apply to the running ferromagnetic part a spray which is a mixture of dry magnetic powder and a gaseous carrier medium whereby the powder adheres to the locations which exhibit defects, and such locations are thereupon detected by a monitoring device which, in turn, controls a source of liquid marking material which is sprayed onto and around the accumulations of powder adhering to the ferromagnetic part so that, when the powder is removed, the marking material surrounds the thus exposed defective portion of the tested part. The patentee further proposes to heat the tested part and to thus bond the powder to the periphery of the part in lieu of the application of a liquid marking material. Each of these proposals is unsatisfactory because the apparatus is complex and all portions of the peripheral surface of a tested part are not moved to optimum positions with reference to the poles of the electromagnet or electromagnets.

OBJECTS AND SUMMARY OF THE INVENTION

An object of the invention is to provide a novel and improved method of continuously testing ferromagnetic parts for the presence or absence of defects in such a way that a single pass through a single testing station suffices to reliably detect the presence of defects (if any) and to allow for elimination of defects or for discarding of overly defective workpieces.

Another object of the invention is to provide a method of stray field magnetic testing which ensures that each and every portion of the peripheral surface of the tested part is monitored to the same extent.

A further object of the invention is to provide a method which can be applied for the testing of continuous ferromagnetic parts and/or for the testing of discontinuous (composite) parts or discrete workpieces.

An additional object of the invention is to provide a novel and improved apparatus for the practice of the above outlined method.

Still another object of the invention is to provide the apparatus with novel and improved means for effecting a relative movement between the tested part and the magnet or magnets which are used to set up the magnetic field.

Another object of the invention is to provide the apparatus with novel and improved means for ensuring predictable contact between magnetic powder and the defective portions of a ferromagnetic part.

A further object of the invention is to provide the apparatus with novel and improved means for reliably detecting longitudinally and/or transversely extending defects in the peripheral surface of a ferromagnetic part.

Another object of the invention is to provide novel and improved means for preventing contamination of the apparatus and/or of the surrounding area with magnetic powder.

One feature of the invention resides in the provision of a method of stray field or stray flux magnetic testing an elongated ferromagnetic part (such as an elongated iron or steel rod or bar) for defects. The method comprises the steps of establishing and maintaining a magnetic field, rotating the part to be tested in the magnetic field about an axis which extends in the longitudinal direction of the part whereby a stray magnetic flux develops at the locations of defects (if any) on the rotating part, and establishing and maintaining a supply of pulverulent magnetic material adjacent to the rotating part so that the stray flux or fluxes (if any) attract pulverulent material which thereby pinpoints the locations of defects. The pulverulent material is preferably dry, and the step of establishing and maintaining a m;agnetic field preferably includes placing the poles of one or more electromagnets close to but out of actual contact with the rotating part. The step of establishing and maintaining a supply of pulverulent magnetic material preferably includes establishing a cushion or bed of such pulverulent material at a level below and in contact with the rotating part. The method preferably further comprises the step of advancing the part to be tested (e.g., a continuous rod or bar or a composite rod or bar consisting of a succession of discrete elongated sections) longitudinally, with reference to the magnetic field and with reference to the supply of pulverulent magnetic material.

The method can further comprise the step of fixing the attracted pulverulent material to the respective (defective) portion of the rotating and longitudinally advancing part or of applying a coloring agent around each accumulation of pulverulent material on the rotating and longitudinally advancing part to thus provide a more or less lasting identification of the respective defect.

If the part is an elongated cylinder, it is preferably rotated about its longitudinal axis. The advancing step preferably comprises moving the rotating part along an at least substantially horizontal path (i.e., along a path whose horizontal component is longer than its vertical component), and the step of establishing and maintaining a supply of pulverulent magnetic material preferably comprises establishing a cushion or bed of such material at a level below and in contact with successive longitudinally and circumferentially extending increments of the periphery of the rotating and axially advancing part. The arrangement is preferably such that the bed or cushion of pulverulent material is in contact with a helically extending strip of the peripheral surface of the part and the neighboring convolutions of such strip touch or even overlap each other.

Another feature of the invention resides in the provision of an apparatus for stray field or stray flux magnetic testing of an elongated ferromagnetic part for the presence or absence of defects. The apparatus comprises magnet means for establishing and maintaining a magnetic field, drive means for rotating the part to be tested in the magnetic field about an axis which extends in the longitudinal direction of the part (such axis preferably constitutes the longitudinal axis of a cylindrical rod-shaped part) whereby a stray magnetic flux develops at the location of each defect (if any) in the rotating part, and marking means for establishing and maintaining a supply of dry pulverulent magnetic material adjacent to the rotating part so that the stray flux or fluxes, if any, attract pulverulent material which thereby pinpoints the locations of defects.

The drive means preferably comprises means for advancing the part to be tested longitudinally along an elongated and preferably at least substantially horizontal path. The magnet means has a pair of poles which establish a magnetic field primarily in the lower portion of the part which advances along and rotates in such path. The drive means is preferably arranged to effect a revolution of the part while an increment of such part advances through a predetermined distance along the aforementioned path. The length of the poles, as considered in the longitudinal direction of the path, matches or exceeds the predetermined distance. The poles are preferably spaced apart from one another, as considered in the circumferential direction of the rotating part, and the marking means is arranged to establish and maintain a supply of pulverulent magnetic material adjacent to one of these poles. The poles are elongated, as considered in the longitudinal direction of the path, and the means for establishing and maintaining a magnetic field preferably further comprises a second magnet having two additional poles which are spaced apart from one another, as considered in the longitudinal direction of the path, and are adjacent to the one pole, i.e., to the cushion of pulverulent magnetic material. In accordance with a presently preferred embodiment of the apparatus, the magnets are electromagnets and the apparatus preferably further comprises means for supplying to the two electromagnets current with a phase shift of 90°. A body of nonmagnetic material can be placed between the poles of the first magnet to avoid the development of a magnetic short circuit between its poles.

The marking means can comprise a source of dry pulverulent magnetic material and one or more conduits for conveying pulverulent material from the source into the magnetic field, preferably to one pole of the first magnet. Alternatively, the marking means can comprise a source of dry pulverulent magnetic material and a rotary element (e.g., a toothed metering wheel) which serves to advance pulverulent material from the source to one pole of the first magnet. The supply of pulverulent magnetic material automatically accumulates at the other pole of the first magnet if the other pole is located downstream of the one pole, as considered in the direction of rotation of the ferromagnetic part. This is due to the establishment of a magnetic field between the two poles of the first magnet and to entrainment of pulverulent magnetic material from the one pole to the other pole of the first magnet by the rotating ferromagnetic part.

The drive means can comprise a plurality of driven rolls whose axes make oblique angles with the axis of rotation of the ferromagmetic part. This enables such rolls to move the ferromagnetic part longitudinally as well as to simultaneously rotate such part. The rolls preferably have elastomeric portions which contact the ferromagnetic part, and such portions can be made of hard rubber or of a suitable elastomeric synthetic plastic material. It is also possible to use rolls which constitute wheels having inflated tires serving to contact the ferromagnetic part.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is a schematic elevational view of certain parts of an apparatus which can be utilized for the practice of the improved method;

FIG. 4 illustrates the electromagnet of FIGS. 2-3 and a portion of the means for establishing and maintaining a supply of pulverulent magnetic material adjacent to one pole of the electromagnet;

FIG. 5 is a side elevational view of the structure which is shown in FIG. 4 and depicts the relationship between the distance which a point at the periphery of the advancing part covers during one revolution of the ferromagnetic part and the length of the poles of the electromagnet;

FIG. 6 illustrates the electromagnet of FIGS. 2-5 and modified means for establishing and maintaining a supply of pulverulent magnetic material;

FIG. 7 illustrates a further apparatus with means for intercepting and recirculating the pulverulent magnetic material;

FIG. 8 is a side elevational view of a portion of an apparatus with two electromagnets;

FIG. 9 is an end elevational view of the structure which is shown in FIG. 8;

FIG. 11 is a somewhat schematic end elevational view of a complete apparatus for the practice of the improved method; and FIG. 12 is a side elevational view of the apparatus which is shown in FIG. 11.

DESCRIPTION OF THE PREFERRED EMBODIMENTS

Figure 3:
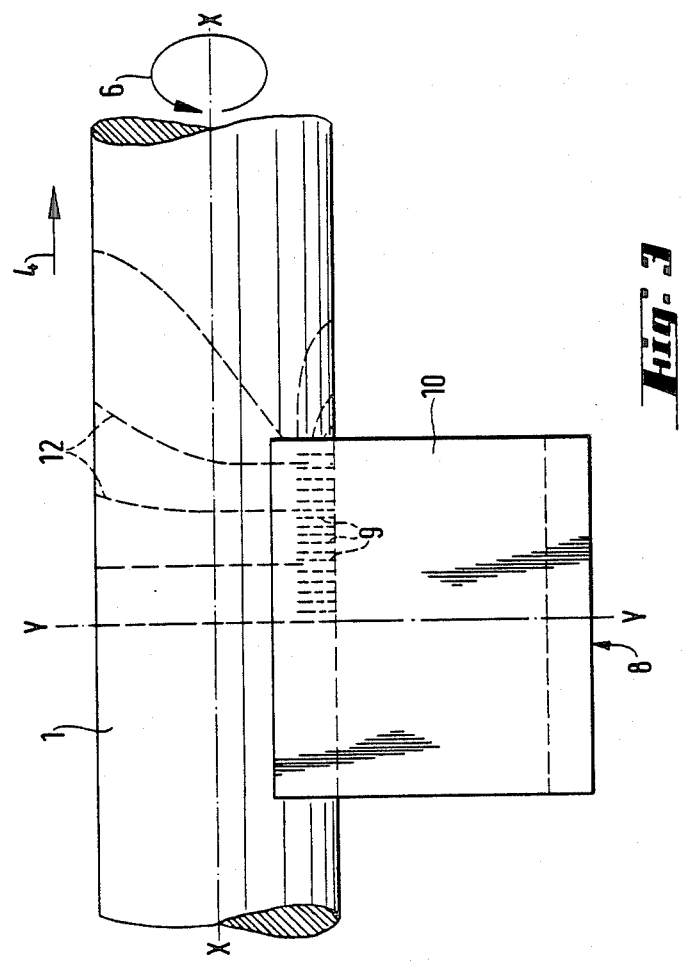
FIG. 3 is a side elevational view of the electromagnet.

FIG. 1 shows a ferromagnetic part 1 which is an elongated rod having a circular cross-sectional outline and advancing longitudinally in the direction of arrow 4. At the same time, the part 1 rotates about its longitudinal axis X—X as indicated by the arrow 6 so that each point at the periphery of the part 1 travels along a helical path P (indicated by a broken line). The drive means for rotating the part 1 about the axis X—X and for simultaneously advancing the part 1 longitudinally in the direction of arrow 4 comprises a first set 2 of driven rolls 5 ahead of the testing station T and a second set 3 of driven rolls 5 downstream of the station T, as considered in the direction of arrow 4. The exact orientation of the rolls 5 constituting the sets 2 and 3 with reference to the elongated (preferably horizontal or substantially horizontal) path of longitudinal movement of the part 1 is shown in greater detail in FIGS. 11 and 12. While FIG. 1 shows a part 1 with a circular outline, the improved apparatus can be used with equal or similar advantage for the testing of elongated ferromagnetic parts having an oval, partly circular or oval and partly polygonal outline, or a strictly polygonal outline. All that counts is to ensure that the drive means is designed to rotate the part to be tested about an axis which extends in the longitudinal direction of the part and that the drive means be preferably also capable of advancing the part longitudinally.

The apparatus further comprises means for establishing and maintaining a cushion or bed 7 of pulverulent magnetic material adjacent to the path of the rotating and longitudinally advancing part 1 at the testing station T (i.e., between the sets 2 and 3 of rolls 5) as well as at least one U-shaped electromagnet 8 which is installed at the testing station T and serves to establish and maintain a magnetic field so that a stray magnetic flux automatically develops at the locations of defects (if any) on the moving part 1. The poles of the electromagnet 8 extend in the longitudinal direction of the part 1, i.e., in a direction from the rolls 5 forming the set 2 toward the rolls 5 which form the set 3. This can be readily seen in FIGS. 2 and 3 which illustrate the single yoke-like or U-shaped electromagnet 8 in greater detail. Pulverulent material which adheres to the defective portions of the part 1 can be more or less permanently bonded to the peripheral surface of the part 1 or it may be identified by a marking liquid in a manner as disclosed in the aforediscussed U.S. Pat. No. 3,614,604 to Reinshagen. The disclosure of Reinshagen is incorporated herein by reference. If a liquefied marking medium or agent is used, the pulverulent material directly overlying the defective portion of the part 1 is thereupon removed in a manner to be described with reference to FIGS. 11 and 12 so that the dried marking medium surrounds the defective portion and provides a readily detectable identification of the defect or defects.

Figure 2:
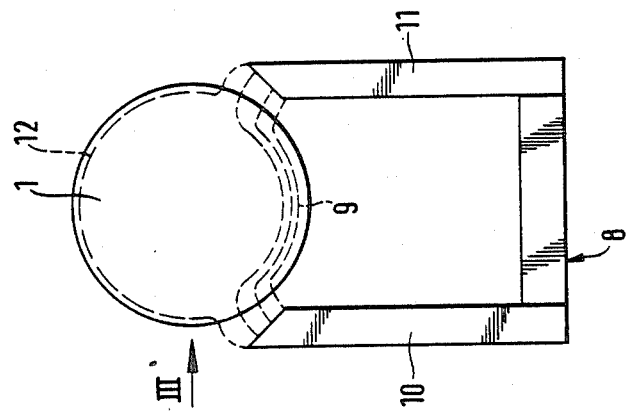
FIG. 2 is an end elevational view of an electromagnet which can be utilized in the apparatus of the present invention.

FIGS. 2 and 3 show that the electromagnet 8 comprises two elongated parallel legs 10 and 11 which extend in parallelism with the axis of the part 1, i.e., in the longitudinal direction of the path which is defined by the sets 2 and 3 of rolls 5. The main magnetic field between the elongated poles of the legs 10 and 11 is shown at 9 and the minor or subordinate flux is shown at 12. The exciting windings (see the windings 19 and 20 in FIG. 10) are omitted in FIGS. 2 and 3 for the sake of clarity. The main field 9 extends along the shortest path between the poles of the legs 10 and 11 and along the lower portion of the periphery of the part 1. The minor or subordinate flux 12 is much less pronounced than the field 9 but it suffices to develop a stray field in the region of each defect and ensure that accumulations of pulverulent magnetic material are adequately attracted to the respective (defective) portions of the part 1. Such pulverulent material is withdrawn from the cushion 7 (see particularly FIGS. 4 and 5) which accumulates primarily in the region of the pole of the leg 10, i.e., of that leg which is located downstream of the other leg as considered in the direction (arrow 6) of rotation of the ferromagnetic part 1 about its axis.

For the sake of clarity, FIG. 3 merely shows the right-hand portion of the main magnetic field 9 and only a part of the minor or subordinate flux 12; the other half of the main field 9 is mirror symmetrical to the illustrated half with reference to a plane Y—Y which is normal to the axis X—X of the part 1 and halves the electromagnet 8.

The means for establishing and maintaining the cushion 7 in the region of the pole of the leg 10 comprises one or more conduits 13 (see FIGS. 4 and 5) which supply streams of dry pulverulent magnetic material from a main source (such as 16 in FIG. 7) of dry magnetic material in a gaseous carrier medium. The cushion 7 is established and maintained in the region of the pole of the downstream leg 10 of the electromagnet 8 because the ferromagnetic part 1 is caused to rotate in the direction of arrow 6. The outline of the cushion 7 (as viewed in the longitudinal direction of the ferromagnetic part 1) can be seen in FIG. 5, and the outline of such cushion as considered in the circumferential direction of the part 1 can be seen in FIG. 4. The accumulation of pulverulent magnetic material is more pronounced at the downstream side of the leg 10 (as considered in the direction of arrow 4) because the part 1 moves in such direction.

When the testing apparatus is in actual use, i.e., when the ferromagnetic part 1 rotates and simultaneously moves longitudinally in directions which are respectively indicated by the arrows 6 and 4, the conduits 13 ensure the establishment of a more or less stationary and constant cushion 7 which accumulates in the region of the pole of the leg 10 and is in contact with the underside of the moving part 1. The exciting windings 19, 20 for the electromagnet 8 are connected to a source of electrical energy so that the electromagnet 8 invariably develops the main magnetic field 9 and occasionally develops a minor or subordinate magnetic flux 12 and a stray flux whenever a defective portion of the ferromagnetic part 1 advances between the poles of the legs 10 and 11. Each stray flux 12 causes the formation of a streak or an analogous deposition of pulverulent magnetic material which thus pinpoints the location of the defect and allows for its elimination when such defect reaches the upper side of the longitudinally advancing and rotating part 1. The exact manner of eliminating defects forms no part of the present invention. Alternatively, and as already mentioned above, pulverulent magnetic material overlying a stray flux 12 and the adjacent portion of the periphery of the ferromagnetic part 1 are coated with a liquefied marking medium which is thereupon dried prior to removal of the pulverulent magnetic material so that the defective portion of the part 1 is readily identifiable for carrying out a remedial action at a later stage, i.e., outside of the testing apparatus.

FIG. 5 shows that the length B of the poles of the legs 10 and 11 of the electromagnet 8 at least matches but preferably exceeds the distance V which any point at the periphery of the part 1 covers in the longitudinal direction of the path for such part while it completes a full revolution about the axis X—X. In other words, any selected portion of the peripheral surface of the ferromagnetic part 1 completes a full revolution about the axis X—X before such selected portion advances from the left-hand end to the right-hand end of the magnet 8, as viewed in FIG. 5. This ensures that each and every portion of the peripheral surface of the part 1 is examined or monitored to the same extent and that each and every portion comes in contact with the cushion 7 before it advances beyond the electromagnet 8 and the magnetic field 9. Consequently, the improved testing apparatus ensures the detection of all defects which warrant detection as a result of a single pass of the part 1 through the testing station T. In addition, such mode of relating the speed of longitudinal and angular movements of the part 1 to the length of the electromagnet 8 ensures that the stray fluxes 12 which develop along the defective portions of the part 1 will remain effective for an interval of time which suffices to allow for immediate detection and elimination of defects while they are accessible at the upper side of the part 1 or for a more or less permanent or longer-lasting identification of defects for the purpose of elimination or other mode of evaluation downstream of the testing apparatus.

FIG. 6 shows a different means for establishing and maintaining a supply of dry pulverulent magnetic material adjacent to the pole of the leg 10. The source (e.g., an elongated magazine) of dry pulverulent magnetic material is shown at 116, and this source is adjacent to a downwardly sloping ramp 15 which receives a layer of pulverulent material under the action of a rotary element here shown as a toothed metering roller 14 which is driven in a counterclockwise direction, as viewed in FIG. 6. The axial length of the roller 14 equals or approximates the length B of the electromagnet 8. The ramp 15 can be made of a suitable metallic or other sheet material and its lower end portion delivers successive increments of the layer thereon into the range of the elongated pole of the leg 11. The pulverulent material adheres to the underside of the rotating and longitudinally advancing part 1 and forms the cushion 7 along the pole of the leg 10.

Referring to FIG. 7, there is shown a portion of a testing apparatus which comprises the electromagnet 8 of FIGS. 2 to 6 and the aforementioned source 16 of dry pulverulent magnetic material. The source 16 is or comprises a funnel-shaped magazine at a level below the electromagnet 8 and admits pulverulent material to a plurality of conduits 13 (only one shown in FIG. 7) which deliver a mixture of pulverulent material and a gaseous carrier medium (the source of the gaseous carrier medium is not specifically shown) in a manner as shown in FIG. 5. The surplus of pulverulent material descends back into the source 16, and such material is recirculated by the conduits 13 so that the operation is economical and the likelihood of contaminating the apparatus and/or the surrounding area with magnetic powder is reduced to a minimum. The likelihood of contamination is reduced still further if the apparatus is equipped with a jacket or shroud 17 which can constitute an upward extension of the source 16 and surrounds the major part of the path for the ferromagnetic part 1. When the testing operation is completed, at least the major part of the mass of pulverulent material which forms the cushion 7 automatically descends into the source 16.

The U-shaped electromagnets which are shown in FIGS. 2 to 7 effect a transverse magnetizing of the lower portion of the part 1 so that such magnets allow for reliable and complete detection of longitudinally extending defects. In order to further ensure an equally reliable detection of all transversely (circumferentially) extending defects, the improved apparatus is preferably further provided with a second U-shaped electromagnet 18 which is shown in FIGS. 8 and 9 and whose poles are spaced apart from one another as considered in the direction of the axis X—X of the part 1. These poles are adjacent to the longitudinally extending pole of the leg 10 of the electromagnet 8, i.e., they are located in the region of that pole of the electromagnet 8 which is adjacent to the cushion 7 of pulverulent magnetic material. It will be noted that in FIGS. 8 and 9 the part 1 rotates in a counterclockwise direction. Simultaneous longitudinal and circumferential magnetizing of the part 1 ensures simultaneous detection of all longitudinally and circumferentially extending defects in a single operation. FIG. 8 shows that the legs 18a and 18b of the second electromagnet 18 can flank the leg 10 of the electromagnet 8.

The energy source 50 which is connected with the exciting windings of the electromagnets 8 and 18 is designed to supply to the electromagnet 8 current with a 90° phase shift relative to the current for the electromagnet 18. This is desirable and advantageous because it ensures that the defects are properly pinpointed by streaks of pulverulent magnetic material irrespective of the direction of longitudinal advancement of the part 1. The latter can constitute a solid cylinder (as shown in FIGS. 1 to 8) or a tubular body (FIGS. 8 and 9).

The shroud or jacket 17 of FIGS. 7 and 9 affords access to a portion of the peripheral surface of the part 1 so as to allow for immediate visual detection of a defect and for immediate remedial action or for the application of the aforediscussed liquefied marking medium (e.g., with a hand sprayer).

Figure 10:
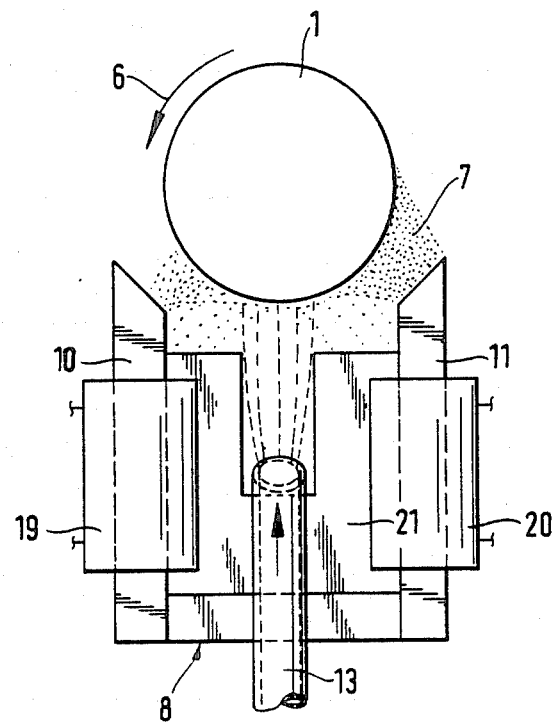
FIG. 10 illustrates an electromagnet and a body of nonmagnetic material between its poles.

FIG. 10 shows a portion of a further testing apparatus wherein the electromagnet 8 surrounds and confines a body 21 of nonmagnetic filler material. Such material reduces the likelihood of a magnetic short circuit between the legs 10 and 11 of the electromagnet 8. These legs respectively carry exciting windings 19 and 20. The central portion of the body 21 of nonmagnetic material defines a longitudinally extending channel for reception of pulverulent magnetic material from the conduit or conduits 13. The absence of a magnetic short circuit reduces the likelihood of bridging of pulverulent magnetic material at the testing station.

Referring to FIGS. 11 and 12, there is shown one form of a complete apparatus which can be utilized for the practice of the improved method. The ferromagnetic part 1 is advanced longitudinally (arrow 4) and is simultaneously rotated about its axis X—X (arrow 6) by the two sets 2 and 3 of rolls 5 (only one roll of each of these sets is actually shownl whose axes make oblique angles with the axis X—X. The unit defining the testing station is denoted by the character 22. The rolls 5 are or can be formed with elastic rims 5a which is desirable on several grounds. Thus, such rolls are less likely to damage the peripheral surface of the part 1 and they can be used for longitudinal advancement and simultaneous rotation of workpieces (e.g., semifinished goods made of steel or other ferromagnetic material) having a circular, oval, square or other polygonal outline. Furthermore, the utilization of rolls with peripheral portions 5a made of a suitable elastomeric material contributes to a reduction of noise during transport of the parts to be tested. For example, the rolls 5 can have rims 5a which are made of hard rubber or an elastomeric synthetic plastic material. It is also possible to employ rolls or wheels with pneumatic tires 5a which are filled with air or another gaseous fluid.

The magnet 8 or the magnets 8 and 18 are installed in the lower portion of the unit 22 in the same way as described in connection with FIGS. 2 to 10, and the unit 22 further accommodates the aforedescribed means for establishing and maintaining a cushion 7 of dry pulverulent magnetic material adjacent to the pole of the downstream leg 10 of the electromagnet 8, as viewed in the direction (arrow 6) of rotation of the part 1 about its axis X—X. FIG. 11 further shows a light source 23 (e.g., a lamp which is pivotably mounted on the frame of the unit 22) which illuminates the rotating and longitudinally advancing part 1 so as to allow for immediate visual detection of pinpointed defects. Visual detection can be resorted to in lieu of or in addition to automatic detection by optoelectronic monitoring means (shown schematically at 24) which can include or constitute a suitable camera. A material removing device 25 is provided in or on the frame of the unit 22 to remove pulverulent material which has pinpointed the defects. The material removing means 25 can utilize a grinding machine or the like and can be actuated by hand or in response to signals from the camera 24. The material removing means 25 can also employ one or more chisels (tools) which are designed to remove pulverulent material as well as some material of the tested part 1.

The material removing device 25 can be used in lieu of a device which is designed to provide a longer-lasting or even permanent identification of detected defects, e.g., in the aforedescribed manner of spraying a liquefied marking medium onto the pulverulent material which adheres to a defective portion of the part 1. The hardened marking material surrounds the defective portion of the part 1 and facilitates the detection of such portion at a later stage, i.e., outside of the testing apparatus. More or less permanent identification of defects is desirable whenever the remedial measures are to be carried out outside of the testing apparatus.

The improved apparatus exhibits the advantage that a complete and reliable testing of elongated ferromagnetic parts can be completed during a single pass through the testing station T, that the testing can be completed as a result of advancement of the part to be tested through a single testing station T, and that the apparatus is surprisingly compact and simple. The phantom line 26 denotes in FIG. 11 the plane in which the part 1 is magnetized by the electromagnet 18 and in which or close to which the part 1 is contacted by the cushion 7. The light source 23 illuminates the part 1 in the plane 27 and the camera 24 images the part 1 in the plane 28. Removal of material by the device 25 takes place in the plane 29. As mentioned above, the device 25 can be actuated by an attendant or in response to signals from the camera 24. The application of a liquefied marking medium in the plane 29 can take place in lieu of removal of material by the device 25, and such application of liquefied marking medium can be effected by hand or in response to signals from the camera 24.

Another important advantage of the improved method and apparatus is that the circumstances under which the part 1 is tested are identical for each and every portion of such part so that the likelihood of detection of defects is the same irrespective of the location of such defects, as considered in the circumferential and/or longitudinal direction of the part. This contributes significantly to reliability of the testing operation in spite of the simplicity and compactness of the apparatus.

An additional important advantage of the improved method and apparatus is that the pulverulent magnetic material need not be propelled against the surface of the advancing and rotating part 1. This not only reduces the energy requirements of the apparatus but it also contributes to reliability of the testing operation because the periphery of the part 1 advances and rotates relative to a stationary cushion 7 of pulverulent material whose mass is preferably constant so as to ensure that the circumstances are the same for the testing of each and every portion of the ferromagnetic part. In many conventional testing apparatus, pulverulent magnetic material or an emulsion of such material is propelled against the periphery of the advancing ferromagnetic part which renders it practically impossible to ensure that the propelled material can impinge with equal force and at the same angle upon each and every portion of the part. The angle of impingement must vary if the ferromagnetic part to be tested advances longitudinally past one or more nozzles which spray a dry or an emulsified magnetic material. While the conduit or conduits 13 which are used in the illustrated testing apparatus can also direct dry pulverulent magnetic material against the periphery of the advancing and rotating part 1, they merely serve to replenish the supply of pulverulent material in the cushion 7 so that the angle at which the admitted pulverent material initially impinges upon the part 1 is of no consequence.

The improved method and apparatus exhibit numerous additional advantages. Thus, the testing operation can be carried out while the ferromagnetic part 1 is cold or heated to an elevated temperature. Furthermore, the quantity of pulverulent magnetic material which is used to form the cushion 7 is surprisingly small and the major percentage of such material can be recirculated again and again. The utilization of a relatively small quantity of pulverulent magnetic material is desirable because this reduces the likelihood of contamination of the testing apparatus and of the surrounding area. Moreover, the operation is more economical. Still further, the improved method and apparatus render it possible to test each of a series of relatively short or long ferromagnetic parts all the way from end to end. The detection and marking of the defects are highly reliable because the detection takes place (in the plane 28) in immediate or close proximity of the locus where the defective portion is contacted by pulverulent material forming the cushion 7. The same holds true for the location (plane 29) where (if desired or necessary) the locations of defects are identified by a liquefied marking medium. The output of the improved apparatus is high because each and every part must be tested only once and also because the parts to be tested can be moved continuously and at a relatively high speed.

If a ferromagnetic part is relatively short, it can be tested in the aforedescribed or in a slightly modified apparatus by causing the rolls 5 to merely rotate the short part about its longitudinal axis without any lengthwise movement.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A method of stray flux magnetic testing an elongated ferromagnetic part for defects, comprising the steps of establishing and maintaining a magnetic field; rotating the part to be tested in the magnetic field about an axis which extends in the longitudinal direction of the part whereby a stray magnetic flux develops at the locations of defects in the rotating part; establishing and maintaining a stationary cushion of dry pulverulent magnetic material at a fixed location and in contact with the rotating part so that the stray flux or fluxes, if any, attract such pulverulent material which thereby pinpoints the locations of defects; and advancing the part to be tested longitudinally with reference to the magnetic field and the cushion of pulverulent material.

2. The method of claim 1, said advancing step including moving the part along a predetermined path; and wherein an increment of the part advances along a predetermined portion of the path while the part undergoes a revolution, the magnetic field and the cushion of pulverulent material extending substantially continuously throughout the predetermined portion of the path.

3. The method of claim 1, wherein said step of establishing and maintaining a magnetic field includes placing the poles of at least one magnet close to but out of contact with the rotating part.

4. The method of claim 1, wherein said step of establishing and maintaining a cushion of pulverulent magnetic material includes establishing a cushion of such pulverulent material at a level below and in contact with the rotating part.

5. The method of claim 1, further comprising the step of fixing the attracted pulverulent material to the respective portion of the ferromagnetic part.

6. The method of claim 1, further comprising the step of applying a marking medium around each accumulation of pulverulent material on the rotating part to thus establish a lasting identification of the respective defect.

7. The method of claim 1 of testing a cylindrical part, wherein said rotating step includes rotating the cylindrical part about its longitudinal axis.

8. The method of claim 1, wherein said advancing step includes moving the rotating part along an at least substantially horizontal path and said step of establishing and maintaining a cushion of pulverulent magnetic material comprises establishing a cushion of such material at a level below and in contact with successive longitudinally and circumferentially extending increments of the periphery of the ferromagnetic part.

9. Apparatus for stray flux magnetic testing of an elongated ferromagnetic part for defects, comprising magnet means for establishing and maintaining a magnetic field; drive means for rotating the part to be tested in said magnetic field about an axis which extends in the longitudinal direction of the part whereby a stray magnetic flux develops at the locations of defects in the rotating part, said drive means including means for advancing the part longitudinally along a predetermined path; and marking means for establishing and maintaining a stationary cushion of dry pulverulent magnetic material at a fixed location and in contact with the rotating part so that the stray flux or fluxes, if any, attract such pulverulent material which thereby pinpoints the locations of defects.

10. The apparatus of claim 9, said drive means being arranged to advance an increment of the part along a predetermined portion of the predetermined path while effecting a revolution of the part; and wherein said magnet means includes a pair of poles extending substantially continuously throughout said predetermined portion of said path, said marking means being arranged to establish and maintain a substantially continuous cushion of pulverluent magnetic material throughout said predetermined portion of said path.

11. The apparatus of claim 9, wherein said predetermined path is substantially horizontal and said magnet means has a pair of poles for establishing said magnetic field primarily in the lower portion of the part which rotates in and advances longitudinally along said path.

12. The apparatus of claim 11, wherein said drive means is arranged to effect a revolution of the part while an increment of such part advances through a predetermined distance along said path, the length of said poles, as considered in the longitudinal direction of said path, at least matching said predetermined distance.

13. The apparatus of claim 11, wherein said poles are spaced apart from one another, as considered in the circumferential direction of the rotating part, and said marking means is arranged to establish and maintain said cushion adjacent to one of said poles, said poles being elongated, as considered in the longitudinal direction of said path, and said magnet means further having two additional poles which are spaced apart from one another as considered in the longitudinal direction of said path and are adjacent to said one pole.

14. The apparatus of claim 13, wherein said magnet means comprises a first electromagnet having said pair of poles, a second electromagnet having said additional poles, and means for supplying to said first and second electromagnets currents with a phase shift of 90°.

15. The apparatus of claim 11, further comprising a body of nonmagnetic filler material between said poles.

16. The apparatus of claim 11, wherein said marking means comprises a source of dry pulverulent magnetic material and conduit means for conveying pulverulent material from said source into said magnetic field.

17. The apparatus of claim 16, wherein said conduit means is arranged to convey pulverulent material to one of said poles.

18. The apparatus of claim 9, wherein said magnet means has a pair of poles and said marking means comprises a source of dry pulverulent magnetic material and a rotary element arranged to advance such material from said source to one of said poles.

19. The apparatus of claim 18, wherein said one pole is located upstream of the other of said poles, as considered in the direction of rotation of the ferromagnetic part, and said cushion of pulverulent material is accumulated adjacent to said other pole as a result of the establishment of said magnetic field between said poles and the entrainment of magnetic material from said one pole to said other pole in response to rotation of the ferromagnetic part.

20. The apparatus of claim 9, wherein said drive means includes a plurality of driven rolls whose axes make oblique angles with the axis of rotation of the ferromagnetic part.

21. The apparatus of claim 20, wherein said rolls have part-contacting portions of elastomeric material.

22. The apparatus of claim 21, wherein said elastomeric material is hard rubber.

23. The apparatus of claim 21, wherein said elastomeric material is a synthetic plastic substance.

24. The apparatus of claim 20, wherein said rolls constitute wheels with inflated part-contacting tires.

* * * * *